United States Patent
Templeton et al.

(10) Patent No.: US 11,497,663 B2
(45) Date of Patent: *Nov. 15, 2022

(54) SMART SAFETY KITS

(71) Applicant: Rescue Box, Inc., Southold, NY (US)

(72) Inventors: Steven Templeton, Greenport, NY (US); Michelle Pelletier, Greenport, NY (US)

(73) Assignee: Rescue Box, Inc., Southold, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/897,823

(22) Filed: Jun. 10, 2020

(65) Prior Publication Data

US 2020/0297557 A1 Sep. 24, 2020

Related U.S. Application Data

(63) Continuation-in-part of application No. 16/801,332, filed on Feb. 26, 2020, which is a continuation of application No. 16/056,716, filed on Aug. 7, 2018, now Pat. No. 10,617,577.

(60) Provisional application No. 62/596,486, filed on Dec. 8, 2017, provisional application No. 62/542,024, filed on Aug. 7, 2017.

(51) Int. Cl.
| *A61F 17/00* | (2006.01) |
| *G09B 23/28* | (2006.01) |
| *G16H 40/63* | (2018.01) |
| *G16H 20/17* | (2018.01) |
| *G09B 5/06* | (2006.01) |
| *G16H 20/40* | (2018.01) |
| *G16H 20/13* | (2018.01) |
| *H04L 67/12* | (2022.01) |

(52) U.S. Cl.
CPC ............ *A61F 17/00* (2013.01); *G09B 5/06* (2013.01); *G09B 23/28* (2013.01); *G16H 20/13* (2018.01); *G16H 20/17* (2018.01); *G16H 20/40* (2018.01); *G16H 40/63* (2018.01); *H04L 67/12* (2013.01)

(58) Field of Classification Search
CPC ........ A61F 17/00; G16H 20/17; G16H 20/40; G16H 40/63; G16H 20/13; G09B 5/06; G09B 23/28; H04L 67/12
USPC ...................................................... 434/262
See application file for complete search history.

(56) References Cited

U.S. PATENT DOCUMENTS

| 6,039,467 A | 3/2000 | Holmes |
| 6,454,097 B1 | 9/2002 | Blanco |
| 6,468,210 B1 | 10/2002 | Iliff |

(Continued)

OTHER PUBLICATIONS

International Search Report and Written Opinion issued in PCT/US2018/045504 dated Oct. 3, 2018.

(Continued)

*Primary Examiner* — Robert P Bullington, Esq.
(74) *Attorney, Agent, or Firm* — Carter, DeLuca & Farrell LLP (57) ABSTRACT

A smart safety kit includes one or more medical products, a container configured to receive the medical products therein, an interface coupled to the container, a processor, and a memory. The container and the medicals product are separate and distinct. The memory is coupled to the container and includes instructions stored thereon that, when executed by the processor, cause the interface to communicate step-by-step medical instructions for administering treatment to a patient with the medical products.

22 Claims, 10 Drawing Sheets

(56) References Cited

U.S. PATENT DOCUMENTS

| | | |
|---|---|---|
| 6,475,143 B2 | 11/2002 | Iliff |
| 6,524,241 B2 | 2/2003 | Iliff |
| 6,527,713 B2 | 3/2003 | Iliff |
| 6,569,093 B2 | 5/2003 | Iliff |
| 6,612,985 B2 | 9/2003 | Eiffert et al. |
| 6,730,027 B2 | 5/2004 | Iliff |
| 6,746,399 B2 | 6/2004 | Iliff |
| 6,764,447 B2 | 7/2004 | Iliff |
| 6,771,172 B1 | 8/2004 | Robinson et al. |
| 6,817,980 B2 | 11/2004 | Iliff |
| 6,937,150 B2 | 8/2005 | Medema et al. |
| 7,623,915 B2 | 11/2009 | Sullivan et al. |
| 7,628,275 B2 | 12/2009 | Smith |
| 7,650,181 B2 | 1/2010 | Freeman et al. |
| 7,729,757 B2 | 6/2010 | Parascandola et al. |
| 7,813,800 B2 | 10/2010 | Fleenor et al. |
| 7,945,451 B2 | 5/2011 | Cosentino et al. |
| 7,967,139 B2 | 6/2011 | Brinker |
| 7,978,890 B2 | 7/2011 | Yamagishi et al. |
| 8,019,582 B2 | 9/2011 | Iliff |
| 8,255,225 B2 | 8/2012 | Byford et al. |
| 8,294,570 B2 | 10/2012 | Clawson |
| 8,321,011 B2 | 11/2012 | Parascandola et al. |
| 8,419,650 B2 | 4/2013 | Cosentino et al. |
| 8,438,044 B2 | 5/2013 | Kerrigan et al. |
| 8,521,538 B2 | 8/2013 | Laughery et al. |
| 8,647,123 B1 | 2/2014 | Carter et al. |
| 8,873,719 B2 | 10/2014 | Clawson |
| 8,968,224 B2 | 3/2015 | Halperin et al. |
| 8,971,501 B2 | 3/2015 | Clawson et al. |
| 9,171,543 B2 | 10/2015 | Emerick et al. |
| 9,286,440 B1 | 3/2016 | Carter et al. |
| 9,286,442 B2 | 3/2016 | Csoma et al. |
| 9,319,859 B2 | 4/2016 | Clawson |
| 9,320,677 B2 | 4/2016 | Johnson et al. |
| 9,324,120 B2 | 4/2016 | Braun |
| 9,352,163 B2 | 5/2016 | Amann |
| 9,491,605 B2 | 11/2016 | Clawson |
| 9,516,166 B1 | 12/2016 | Clawson |
| 9,579,516 B2 | 2/2017 | Kaib et al. |
| 9,596,991 B2 | 3/2017 | Choi |
| 9,619,767 B2 | 4/2017 | Braun |
| 9,693,917 B2 | 7/2017 | Freeman |
| 9,730,845 B2 | 8/2017 | Fresco |
| 9,808,636 B2 | 11/2017 | Amann |
| 9,818,402 B2 | 11/2017 | Emerick et al. |
| 9,996,669 B2 | 6/2018 | Goetz et al. |
| 10,058,469 B2 | 8/2018 | Freeman |
| 10,085,900 B2 | 10/2018 | Johnson et al. |
| 10,109,377 B2 | 10/2018 | Shetty et al. |
| 10,124,109 B2 | 11/2018 | Weinstein et al. |
| 10,195,451 B2 | 2/2019 | Barnes et al. |
| 10,201,714 B2 | 2/2019 | Delisle et al. |
| 10,210,742 B2 | 2/2019 | Abbott |
| 10,229,465 B2 | 3/2019 | Braun et al. |
| 10,249,218 B2 | 4/2019 | Bronson et al. |
| 10,617,577 B2 | 4/2020 | Templeton et al. |
| 2005/0015115 A1* | 1/2005 | Sullivan ............... A61B 5/4824 607/5 |
| 2006/0111749 A1 | 5/2006 | Westenskow et al. |
| 2010/0297594 A1 | 11/2010 | Sullivan et al. |
| 2014/0365390 A1* | 12/2014 | Braun .................... G16H 40/20 705/325 |
| 2015/0272825 A1* | 10/2015 | Lim .......................... G07C 9/38 340/5.2 |
| 2017/0304134 A1 | 10/2017 | Freeman |
| 2017/0333722 A1 | 11/2017 | Chang |
| 2018/0125375 A1 | 5/2018 | Tan et al. |
| 2018/0296847 A1 | 10/2018 | Kaib et al. |
| 2018/0308337 A1 | 10/2018 | Freeman et al. |
| 2018/0318160 A1 | 11/2018 | Freeman |
| 2018/0329722 A1 | 11/2018 | Nguyen et al. |
| 2019/0038481 A1 | 2/2019 | Templeton et al. |
| 2019/0117505 A1 | 4/2019 | Freeman et al. |
| 2019/0168009 A1 | 6/2019 | Barnes et al. |
| 2019/0184186 A1 | 6/2019 | Elghazzawi et al. |

OTHER PUBLICATIONS

International Preliminary Report dated Feb. 11, 2020 and Written Opinion completed Sep. 13, 2018 corresponding to counterpart Int'l Patent Application PCT/US18/45504.

International Preliminary Report on Patentability issued by the International Bureau for WIPO in relation to International Application No. PCT/US2018/045504 dated Feb. 11, 2020.

* cited by examiner

SMART SAFETY KITS

CROSS-REFERENCE TO RELATED APPLICATIONS

This application is a continuation-in-part of U.S. patent application Ser. No. 16/801,332, filed Feb. 26, 2020, which is a continuation of U.S. patent application Ser. No. 16/056,716, filed Aug. 7, 2018, now U.S. Pat. No. 10,617,577, which claims the benefit of U.S. Provisional Application No. 62/596,486, filed Dec. 8, 2017 and U.S. Provisional Application No. 62/542,024, filed Aug. 7, 2017, the entire contents of each of which are incorporated by reference herein.

BACKGROUND

Mortality is an immutable characteristic of the living. As a condition of our existence, we are all susceptible to injury, aging, and death. Indeed, medical events such as heart attacks, strokes, allergic reactions, etc. are occurring every second of every day. Research indicates that medical intervention within five minutes of such an event can greatly reduce risks of death or permanent damage. For instance, in a cardiac event, medical intervention within five minutes increases chances of survival by 80 percent.

SUMMARY

Accordingly, the present disclosure describes smart safety kits that interact with users and his/her environment in specific emergency situations to quickly provide step-by-step instructions and/or medical products (e.g., medications) for administering treatment to the user and/or other patients. These smart safety kits include containers for housing these medical products and can include voice and/or visual interfaces for communicating with the user for treating patients having medical events such as chest pain, shortness of breath, allergic reaction, and diabetic complications.

In accordance with one aspect, the present disclosure is directed to smart safety kit comprising one or more medical products, a container configured to receive the medical products therein, an interface coupled to the container, a processor, and a memory coupled to the container. The container and the one or more medical products are separate and distinct. The memory is coupled to the container and includes instructions stored thereon that, when executed by the processor, cause the interface to communicate step-by-step medical instructions for administering treatment to a patient with the medical products.

In some embodiments, the interface may include a display configured to output the medical instructions. The medical instructions may be output on the display with text, images, or combinations thereof.

In certain embodiments, the interface may include a speaker configured to output the medical instructions.

In embodiments, the container may include a lid and a storage compartment. The lid may be configured to selectively enclose the medical products within the storage compartment. The lid may be pivotally coupled to the storage compartment. The lid may be movable relative to the storage compartment from a closed position to an open position. The lid may include a top surface and a bottom surface. The interface may include a display. The bottom surface of the lid may support the display such that the display is concealed when the lid is disposed in the closed position and exposed when the lid is disposed in the open position.

In some embodiments, the smart safety kit may further comprise a power supply that is operatively coupled to the processor to power the processor, the interface, the memory, or combinations thereof.

In certain embodiments, the medical products may include a first independent medical product and a second independent medical product. The container may include an insert that fits in the storage compartment of the container. The insert may define a first cavity and a second cavity. The first cavity may be configured to removably support the first independent medical product therein and the second cavity may be configured to removably support the second independent medical product therein.

In some embodiments, the processor may be configured to communicate with a remote network.

According to yet another aspect, the present disclosure is directed to a method for facilitating medical treatment with a smart safety kit. The method comprises removably supporting one or more independent medical products in a storage compartment of a container of the smart safety kit, and outputting step-by-step medical instructions through an interface of the container for treating a patient with the one or more independent medical products.

The method may further involve receiving an input from a user to communicate with the user. The method may further include outputting one or more steps of the step-by-step medical instructions in response to input received from the user.

In certain aspects of the method, outputting step-by-step medical instructions through the interface of the container may include displaying the step-by-step medical instructions on a display of the interface. Displaying the step-by-step medical instructions may include displaying text, images, or combinations thereof on the display.

In some aspects of the method, outputting step-by-step medical instructions through the interface of the container may involve emitting sound through a speaker of the interface.

In aspects of the method, outputting step-by-step medical instructions through the interface of the container may include emitting sound through a speaker of the interface and displaying the step-by-step medical instructions on a display of the interface.

The method may further involve electrically powering the interface.

The method may further comprise enabling the container to communicate with a remote network.

In one aspect, the method may further comprise illuminating a predetermined portion of the storage compartment to identify the one or more independent medical products.

Other aspects, features, and advantages will be apparent from the description, the drawings, and the claims that follow.

BRIEF DESCRIPTION OF THE DRAWINGS

Embodiments of the present disclosure are described herein with reference to the accompanying drawings, wherein.

DETAILED DESCRIPTION

Embodiments of the presently disclosed smart safety kits are described in detail with reference to the drawings, in which like reference numerals designate identical or corresponding elements in each of the several views. Directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

With reference to FIGS. 1-6, one embodiment of a smart safety kit 10 includes a container 12 formed of any suitable durable material such as ABS and TPE plastics, medical grade. Container 12 includes a lid 14 that is coupled to a storage compartment 16 by any number of hinges 18. Hinges 18 are configured to enable lid 14 to pivot between a closed position (FIGS. 1-4) and an open position (FIG. 5), as indicated by open arrow "O" and close arrow "C." Storage compartment 16 defines a chamber 16a configured to receive an insert system 30. Container 12 further includes a handle 20 for selectively transporting container 12. Container 12 also includes any number of latches 22 that enable lid 14 to selectively couple to storage compartment 16 for securing lid 14 in a closed position (FIGS. 1-4). Container 12 may further include any number of lights 16b (e.g., LEDs). Lights 16b are configured to illuminate chamber 16a of storage compartment 16, or portions thereof.

Container 12 further supports electronics 21 including one or more processors 24, a memory 25 (e.g., which may be internal memory of processor 24), and a power supply 26 (e.g., rechargeable batteries, replaceable batteries, power cord, etc.) and an interface 28 that are operatively coupled together via wireless or wired circuitry 29 (e.g., inductive charger, cables, wires, ribbon cables, etc.).

Processors 24 can include any suitable electrical component such as a microcontroller, printed circuit board (e.g., rigid PCB with SD card and internal memory), wiring, sensors, etc. For instance, processors 24 can include RFID/NFC (active and/or passive) technology; PIC, Arduino, Raspberry Pi microcontroller technology; GPRS (cellular/sms), Wi-Fi 802.11 b/g/n/ac, Bluetooth® BLE 4.0/4.01 communication technology; and/or proximity infrared (PIR), gyroscope, accelerometer, tilt switch, biometric, and/or heart rate/pulse sensor technology.

Memory 25 includes one or more medical instructions stored thereon for effectuating one or more treatment regimens or protocols when executed by processor 24. Memory 25 can include internal memory from which interface 28 displays an instructional video of the medical instructions, which may be step-by-step medical instructions. Memory 25 can include flash memory.

Power supply 26 may include rechargeable batteries, replaceable batteries, photovoltaics, and/or power cord for plug in power. Batteries may have at least 1 year life without charge. Batteries may be smart and/or beep/blink when charge is needed. In some embodiments, power supply may include a 12 volt AC power source with DC uninterruptible backup.

Interface 28 includes a display 28a, speakers 28b, and/or sensors such as microphones 28c and/or cameras 28d. Other sensors may include GPS, altimeters, etc. Display 28a can include a touch screen (e.g., 24-Bit RGB LCD) that enables the user to progress through the medical instructions by touching icons visually presented (text and/or images) on display 28a. Speakers 28b are be wired to processor 24 (e.g., PCB) to play pre-recorded audio. Interface 28 can include a display driver that is compatible with a 24-Bit RGB LCD touch screen, an arm microcontroller, and various other SMD/TH components.

In some embodiments, container 12 can be configured to access one or more databases (e.g., stored on memory 25 and/or in a remote location such as a cloud-based network architecture) which correlate one or more medical conditions with one or more treatment regimens or protocols. The databases can be stand-alone databases or data structures stored in a remote server or other computing device.

In some embodiments, container 12 includes wireless transmitters/receivers for transferring data (real-time and/or stored from memory) and can be controlled or programmed using an app running on an external controller or smart device (not shown) such as a smartphone, portable/fixed computer, tablet, wearable device, etc. connected to a network. For instance, the app can receive and transmit control signals wirelessly (e.g., WIFI signals) and program and/or control processors 24 and/or interface 28 through the internet or other network or server. In certain embodiments, smart safety kit 10, or portions thereof (e.g., container 12) can be configured to be an internet of things (IoT) device that is remotely controlled by a network connection. Wireless communication to/from container 12 may be effectuated through radio frequency, optics, WIFI, BLUETOOTH® (an open wireless protocol for exchanging data over short distances using short length radio waves) from fixed and mobile devices, ZigBee® (a specification for a suite of high level communication protocols using small, low-power digital radios based on the IEEE 802.15.4-2003 standard for wireless personal area networks (WPANs)), etc.

Figure 1:
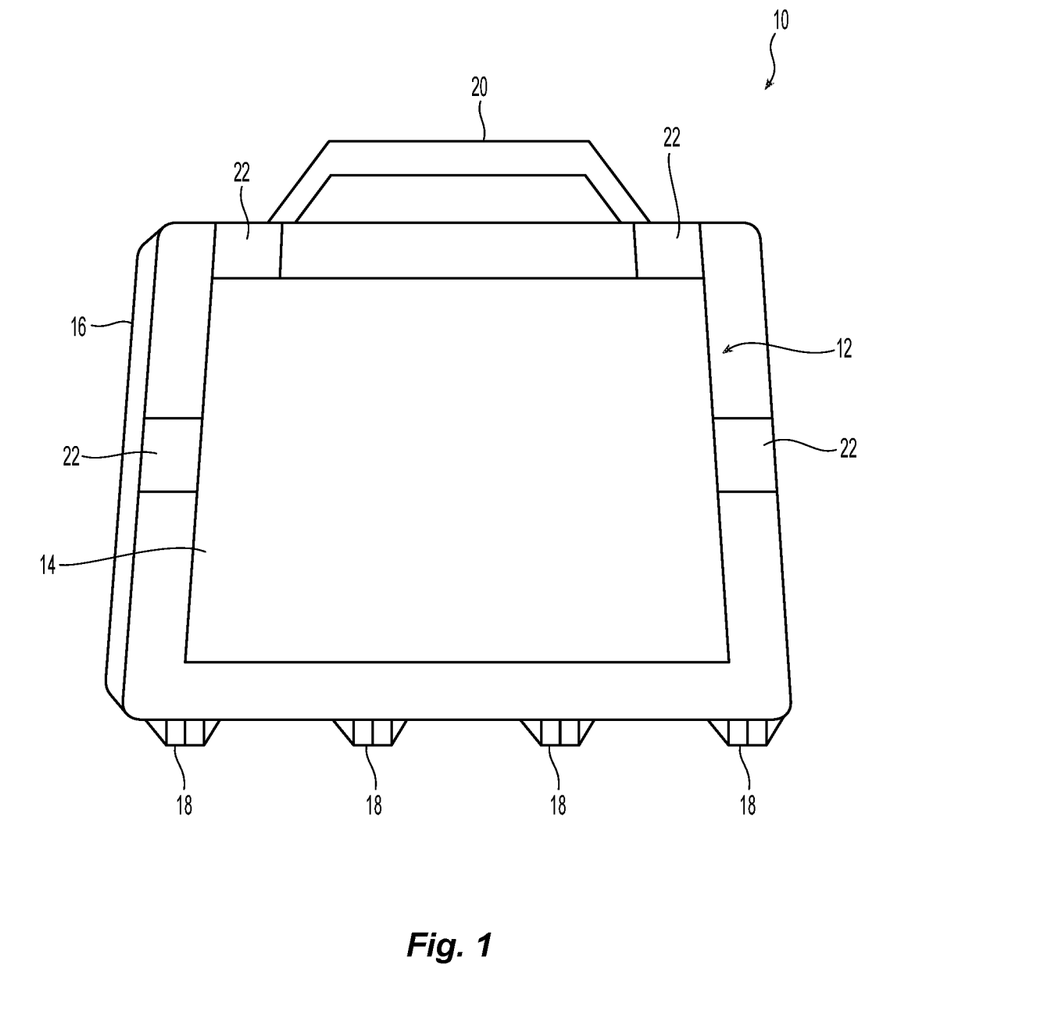
FIG. 1 is a top view of one embodiment of a smart safety kit in accordance with the principles of the present disclosure, the smart safety kit including a container illustrated in a closed position.
Figure 2:
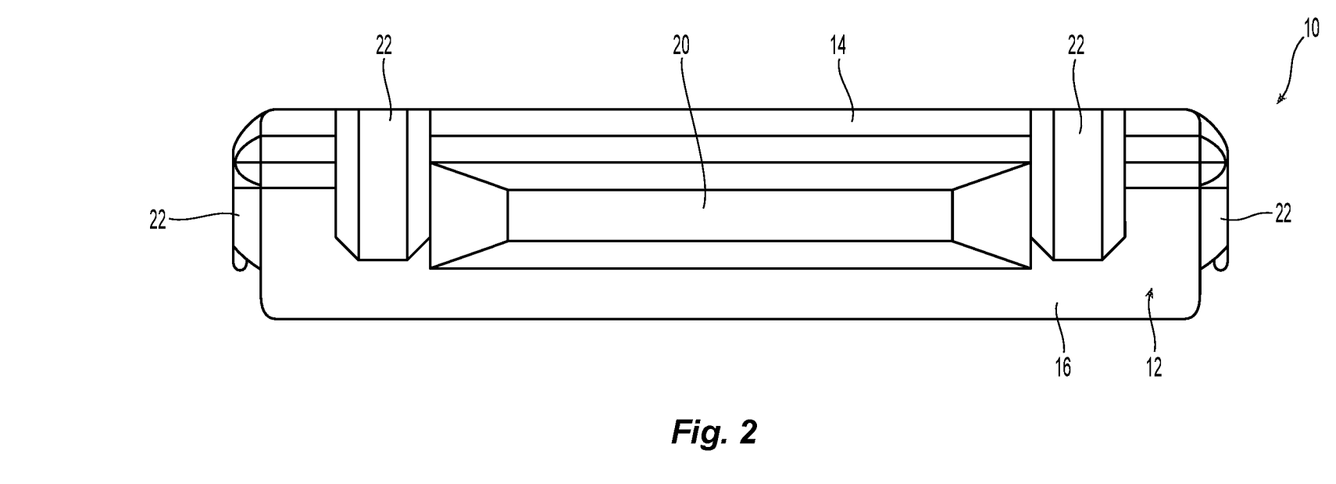
FIG. 2 is a front view of the smart safety kit of FIG. 1.
Figure 3:
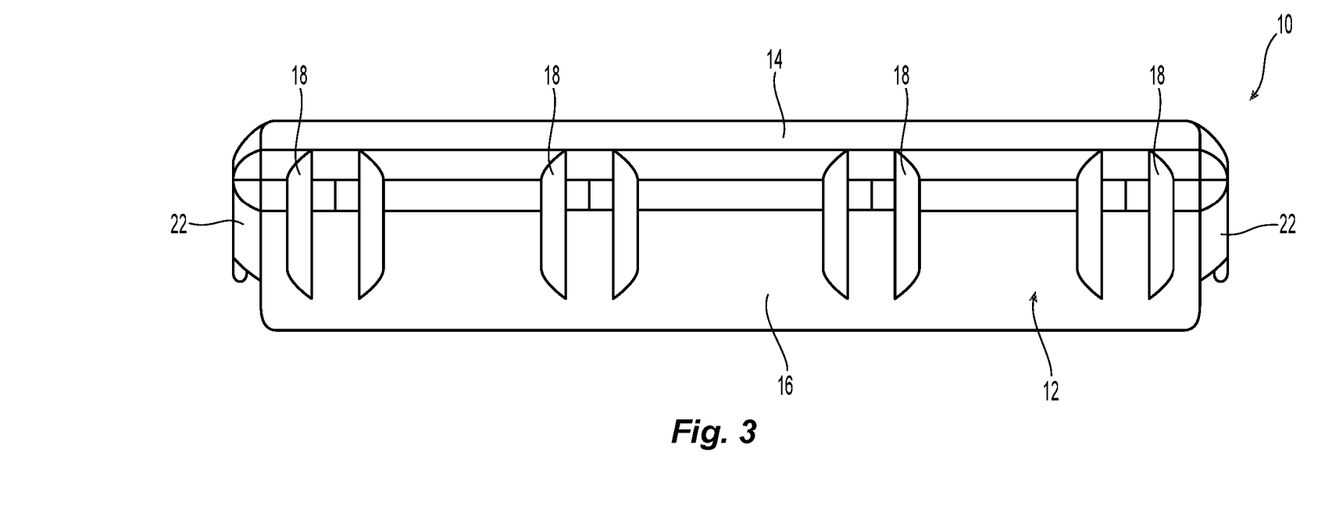
FIG. 3 is a rear view of the smart safety kit of FIGS. 1 and 2.
Figure 4:
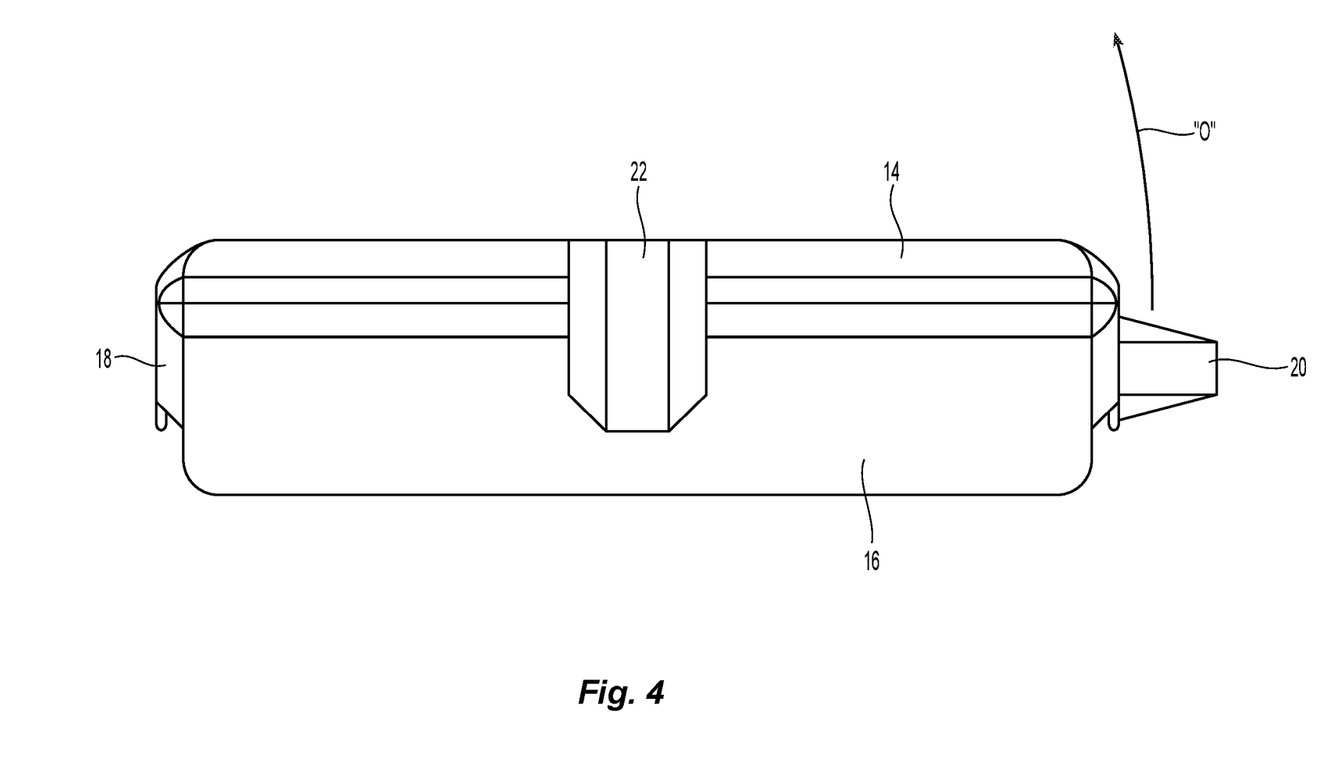
FIG. 4 is a side view of the smart safety kit of FIGS. 1-3.
Figure 5:
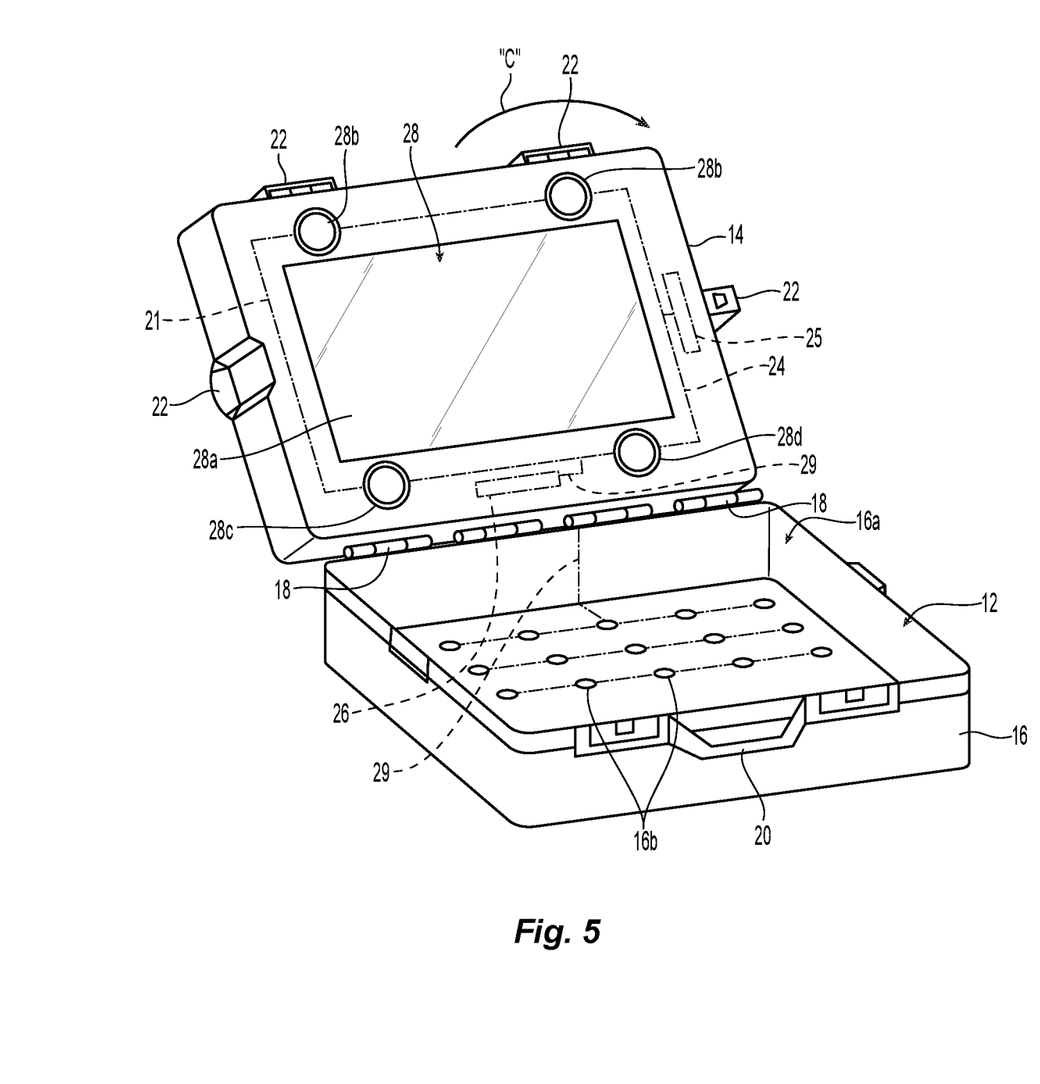
FIG. 5 is a perspective view of the container of the smart safety kit of FIGS. 1-4, the container shown in the open position.
Figure 6:
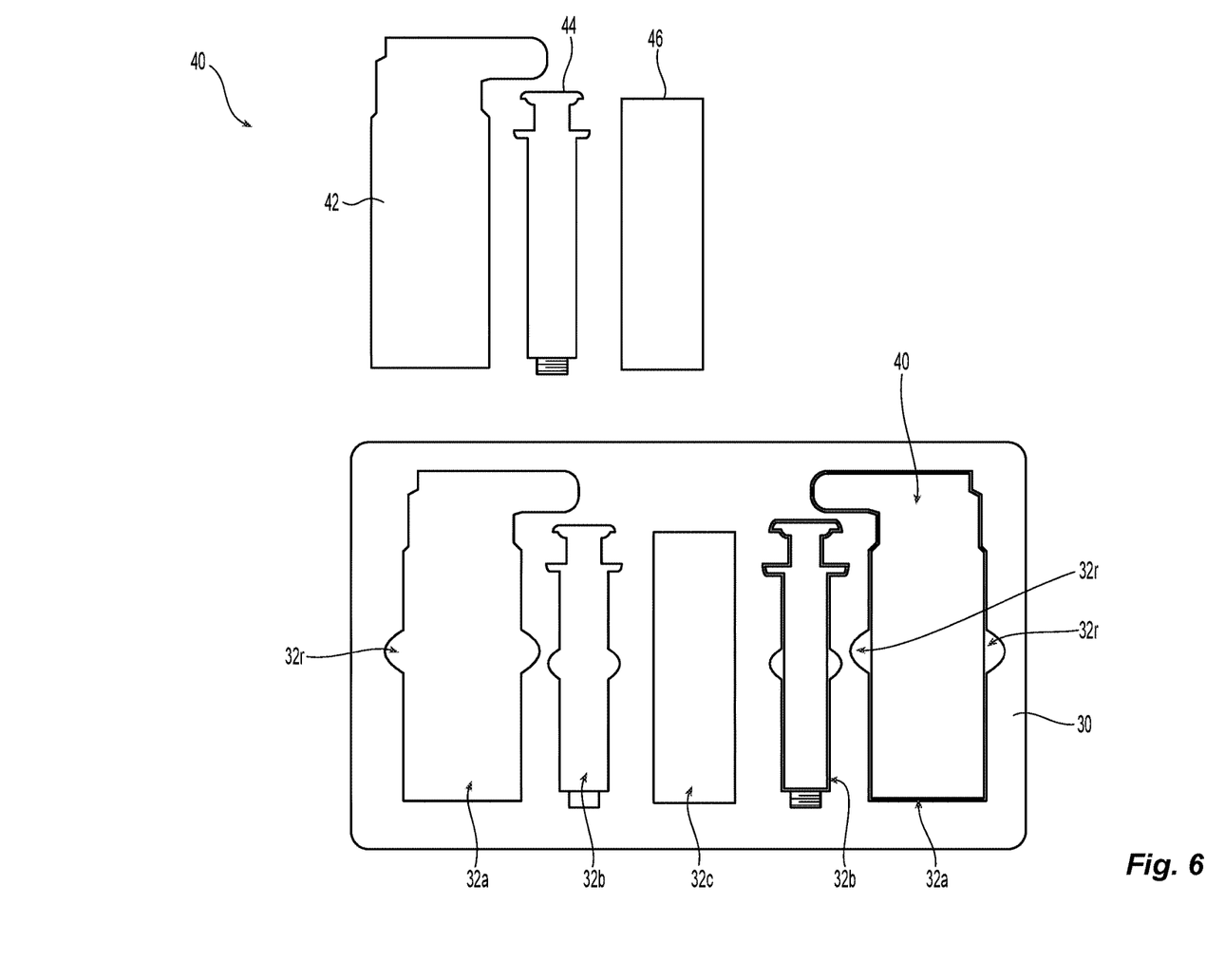
FIG. 6 is a top view of one embodiment of an insert system of the smart safety kit of FIGS. 1-4, the insert system illustrated with various medical products received in cavities defined in an insert of an insert system, and with various medical products separated in other cavities of the insert.

As seen in FIG. 6, an insert 30 of smart safety kit 10, is configured to be received within chamber 16a of storage compartment 16. Insert 30 defines predefined cutouts 32, such as cutouts 32a, 32b, and 32c, which are configured to removably receive independent medical products 40 such as an oxygen booster 42, a syringe 44, and medication 46 therein, respectively.

Figure 7:
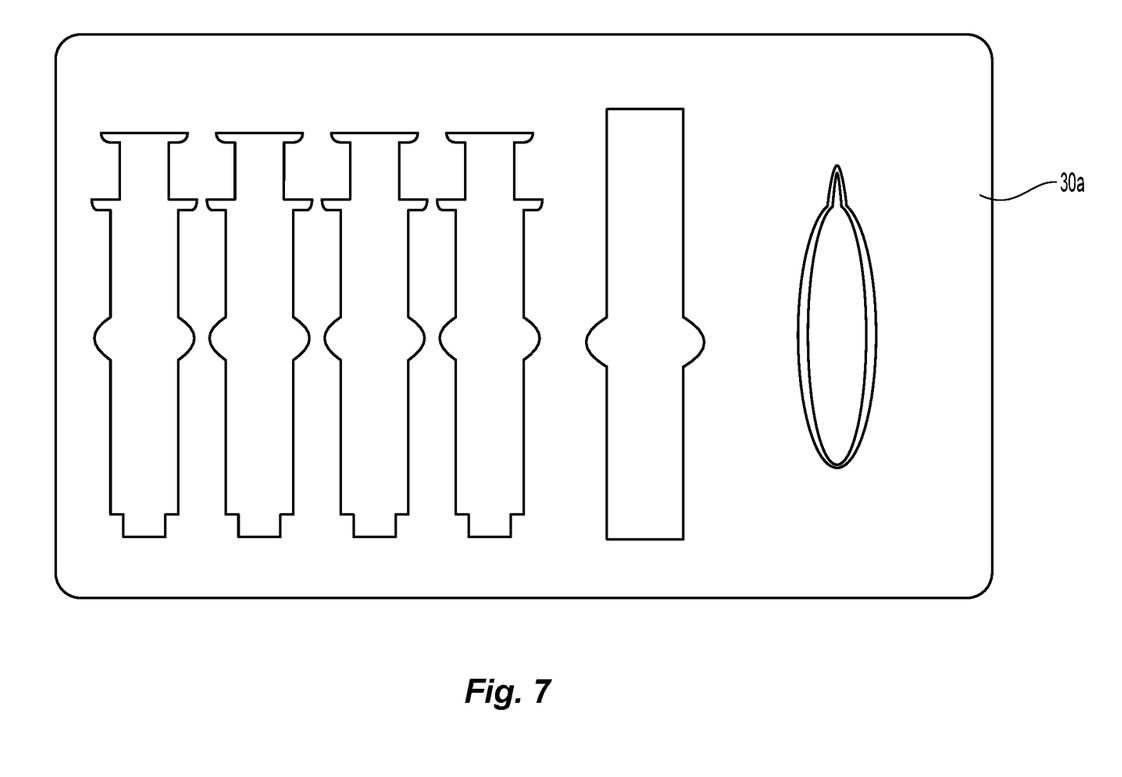
FIG. 7 is a top view of another embodiment of the insert system for use with the smart safety kit of FIGS. 1-4.
Figure 8:
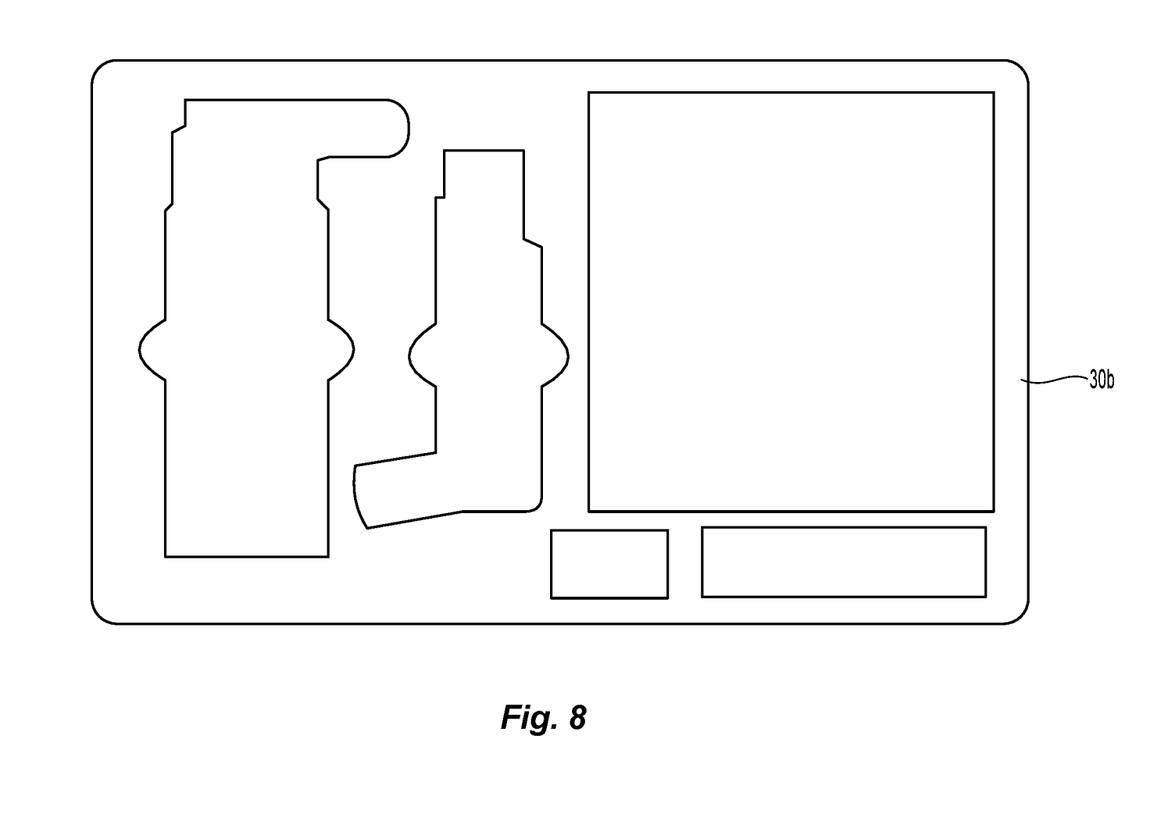
FIG. 8 is a top view of still another embodiment of the insert system for use with the smart safety kit of FIGS. 1-4.
Figure 9:
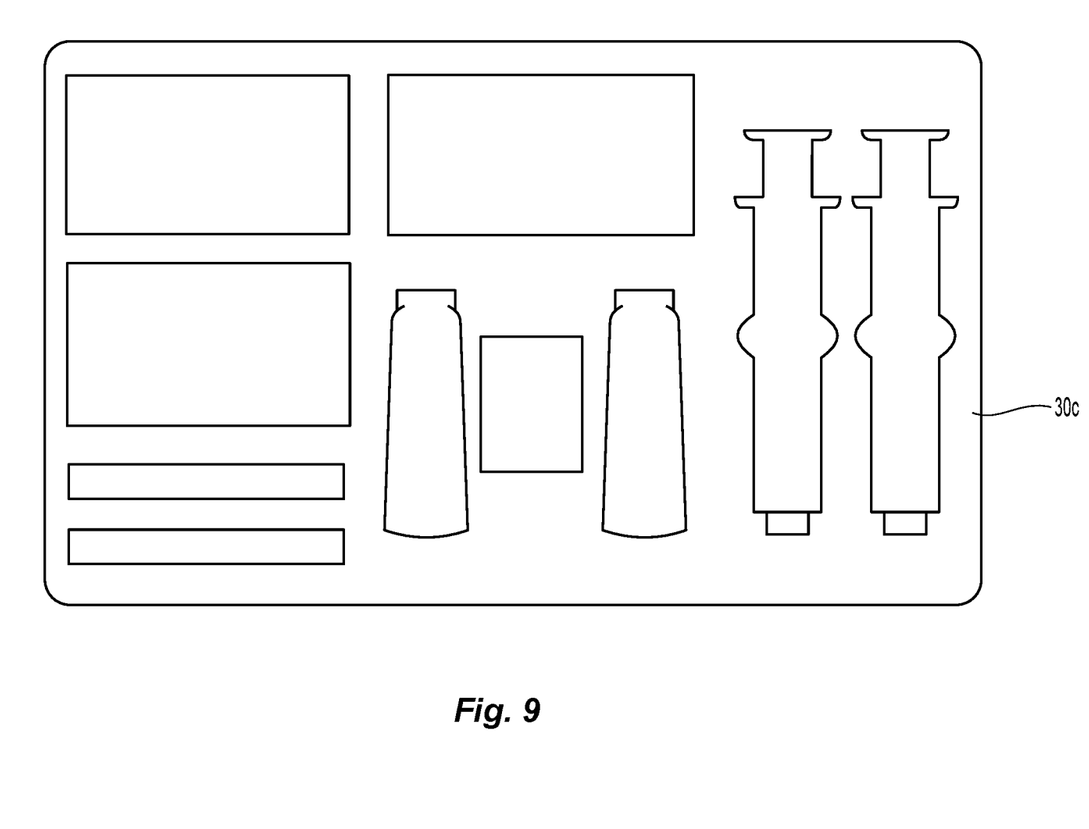
FIG. 9 is a top view of yet another embodiment of the insert system for use with the smart safety kit of FIGS. 1-4.

Insert 30 can have any suitable configuration with any number or configuration of predefined cutouts 32 to accommodate any number of independent medical products 40. Insert 40 may include indicia such as numbers, text, images or the like to help identify the independent medical products 40. For instance, with reference to FIGS. 7-9, inserts 30a, 30b, and 30c are exemplary configurations of inserts that accommodate of variety of different medical products 40. Each insert can be configured to contain any number or arrangement of medical products. Predefined cutouts 32 are configured to receive predetermined medical products. Each cutout 32 can include finger recesses 32r to facilitate removal of a medical product 40 from its respective cutout 32.

One exemplary smart safety kit 10 can include FDA approved medications (with and without prescriptions) that can reduce mortality from serious medical events such as a heart attack, pulmonary disease, and diabetes.

Figure 10:
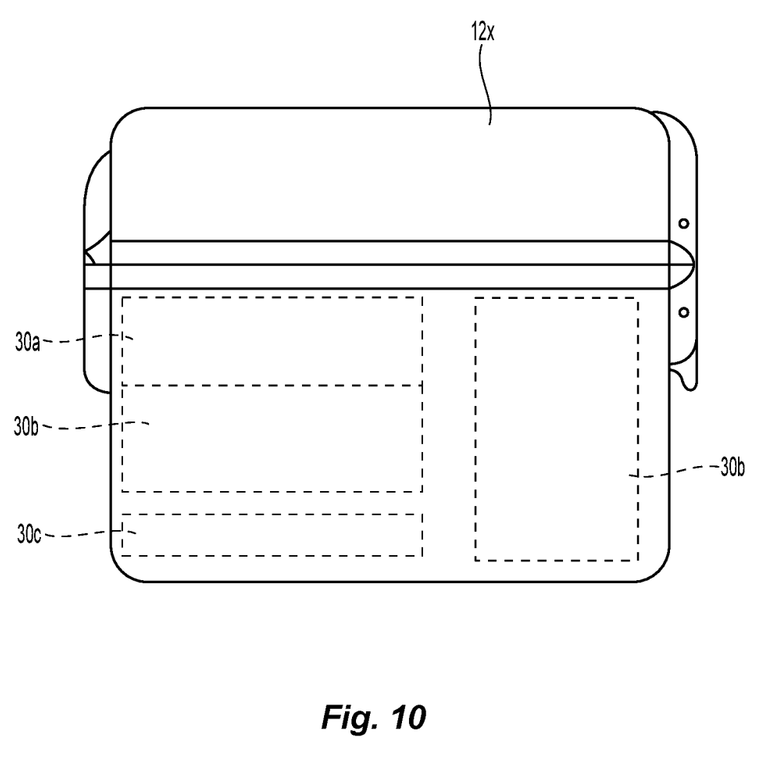
FIG. 10 is a side view of another embodiment of the smart safety kit in accordance with the principles of the present disclosure.

As seen in FIG. 10, smart safety kit 10 can include an enlarged container 12x that is configured to accommodate multiple inserts 30 and a variety of different medical products 40 for treating multiple patients experiencing the same and/or different medical events.

In embodiments, smart safety kits 10 can include software, algorithms, code, platforms, apps, etc. to accommodate and/or provide data aggregation; back-end web admin panel (e.g., CMS that allows different roles with permissions access); master admin access for activity monitoring across platforms/apps to track analytics of trends, demographics, app usage, sales across channels, etc.; CRM of all app users and customers, social login, etc. (e.g., end user access to set up "In Case of Emergency" (ICE) contact that receives SMS as soon as container 12 is opened to alert family of possible distress and contacts 911.)

In certain embodiments, smart safety kits 10 include one or more wearables, for example, a silicone wrist band with embedded RFID/NFC to quickly open container 12 and/or to contact 911 or other ICE contacts.

In some embodiments, smart safety kit 10 can include or cooperate with one or more apps that allow users to interact, customize, and/or manage their smart safety kit 10, contacts, alerts, notifications, messages, registration, etc.

In certain embodiments, backup emergency cards with text/images of the medical instructions can be provided in container 12. In certain embodiments, container 12 may be configured to play a medical instruction presentation through a portal storage device such a DVD, CD, flash drive, etc.

One embodiment of smart safety kit 10 can be a cardio kit in the form of a prescription box or in the form of an over the counter box (OTC). The cardio prescription box can include the following medical products 40: Oxygen (150 inhales), ground Aspirin (325 mg), nitroglycerin tablets (0.4 mg), BETA blocker (50 mg), and Statin (40 mg). The cardio OTC box can include the following medical products 40: Oxygen (150 inhales), ground Aspirin (325 mg), Hawthrown tablet (565 mg), Cramp bark capsules (Viburnum Opulus—375 mg tablet).

Figure 11:
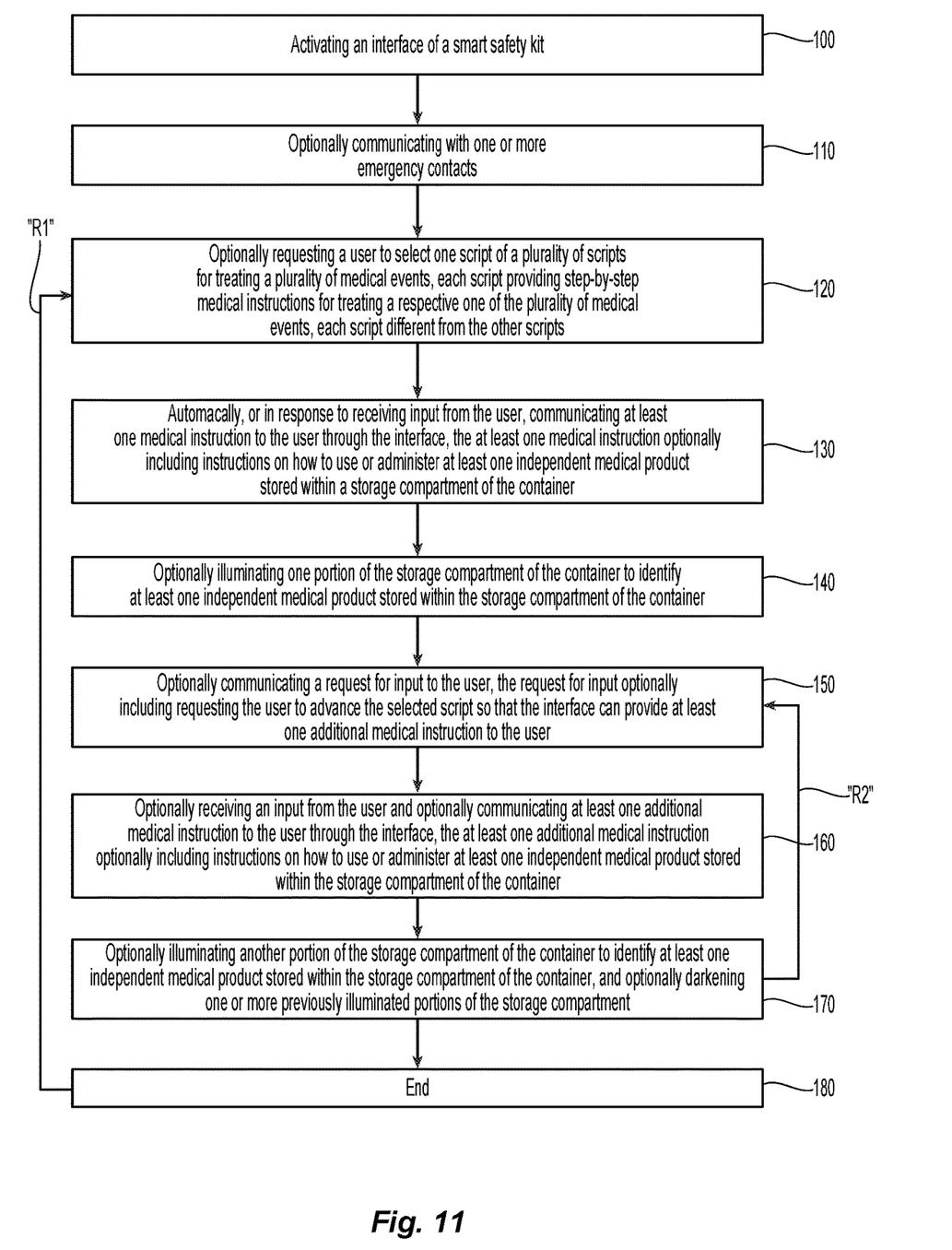
FIG. 11 is an exemplary flowchart representation illustrating the presently disclosed smart safety kit and method of using the same.

Referring now to FIG. 11, with reference to FIGS. 1-10, an exemplary method for facilitating medical treatment with one embodiment of the presently disclosed smart safety kits is provided.

In step 100, an interface 28 of one of the presently disclosed smart safety kits is activated when a container 12 of the smart safety kit is opened; however, the smart safety kit can be activated in any suitable manner, such as by entering a code, pressing a button, scanning an ID, biometrics, etc. The smart safety kit may optionally communicate with (e.g., call, email, text, etc.) one or more emergency contacts (e.g., family, friends, 911, police, EMT, hospital, school administrators, fireman, or other first responders, etc.) that may be stored in memory or accessible through a local or remote network as illustrated by step 110. For example, the smart safety kit can send an email or text message to one or more emergency contacts, which may be pre-input. Such contacts may be provided when installed and/or preprogrammed. In one aspect, the email or text message can include a specific location, such as classroom or "Hot Zone" to help first responders to quickly find a shooter and/or injured party. The smart safety kit may include mapping software that identifies the specific location. For instance, the smart safety kit can include instructions stored on memory, which, when executed by a processor, causes the smart safety kit to send one or more emails or texts to emergency contacts, wherein the emails or text messages include an digital map of the location (e.g., a map of the school, business, building, office, etc. in the public and/or private sector, and which may be any commercial and/or residential buildings or housing, parks, playgrounds, sport arenas, fields, etc., and/or virtually any other suitable predefined area) and a location identifier that corresponds to the specific location of the smart safety kit on the digital map. As used herein, a school can include any private and/or public school, preschool, K-12, college, university, law school, medical school, pharmacy school, etc. As can be appreciated, the digital map can be provided in any suitable format such PDF, JPEG, PNG, GIF, BMP, etc. In one example, the location identifier may be a room number or color indicative of the specific location. The smart safety kit may be configured to receive input through (for example, the interface or other button) from a user such that the instructions, when executed by the processor, cause the smart safety kit to send additional emails and/or texts for updating a location (such as a room number manually input by the user with the smart safety box on the run from an active shooter). In some aspects, the emails and/or texts may be time-stamped to give an idea of trend/location of a shooter and/or injured parties and/or a direction of travel thereof. In aspects, the user may be required to enter an ID and/or a password.

In step 120, although, in certain embodiments, the memory 25 may only store a single script to treat a specific medical event, in some embodiments, the memory 25 may store scripts for different medical events, should one or more of those events occur at any given time. Thus, the interface 28 may prompt a user to select one script of a plurality of scripts (e.g., that may be stored on the memory) for treating a plurality of medical events. For instance, the memory 25 may store a first script with medical instructions to treat a cardic event and a second script to treat an allergy reaction.

In step 130, automatically (e.g., preprogrammed to initiate when the container is opened or activated), or in response to receiving input from the user (e.g., selecting one of a variety of scripts), the interface 28 communicates at least one medical instruction to the user through the interface 28 (e.g., via display 28a, speakers 28b, etc.). The at least one medical instruction may optionally include instructions on how to use or administer at least one independent medical product (e.g., syringe 44) stored within the storage compartment 16 of the container 12 and/or medical instructions that do not involve use of any medical products (e.g., having the patient lie down, instructing a user to provide chest compressions to the patient and/or the Heimlich maneuver, etc.).

For instance, when a user selects one of a plurality of scripts such as a first script for providing treatment for the cardiac event, the interface will communicate with the processor 24 to initiate the step-by-step medical instructions for treating the cardiac event. In embodiments, the interface 28 may be configured to receive input from the user (e.g., touch screen display 28a, microphone 28d, etc.) to stop the script, go backwards, repeat a prompt and/or specific instructions, advance forward, pause, end script, change scripts, etc. In some embodiments, the interface 28 may include buttons or links that access additional information stored on the memory (e.g., background, specifications, contraindications, additional use instructions, warnings, etc.) or accessible through a network, such as the internet, coupled to the interface 28 and/or the processor 24.

In step 140, one portion of the storage compartment 16 of the container 12 may optionally be illuminated by one or more the LEDs 16b of the container 12 to identify at least one independent medical product (e.g., an inhaler 42) stored within the storage compartment 16 of the container 12. The illumination and/or darkening of one or more of the LEDs 16b can correspond to one or more of the medical instructions.

In step 150, after (or simultaneously with) providing one or more medical instructions, the interface 28 can optionally communicate another request for input to the user. The request for input may optionally include a request to advance (e.g., forward or backward) the selected script so that the interface 28 can provide at least one additional medical instruction (e.g., which may be one or more different/same/repeated instruction to the user) from processor 24.

In step 160, an input can be received by the interface 28 (from the user) so that the interface 28/processor 24 communicates at least one additional medical instruction to the user through the interface 28. The at least one additional medical instruction may optionally include instructions on how to use or administer at least one independent medical product stored within the storage compartment of the container 12 and/or medical instructions that do not involve use of any medical products as detailed above with respect to step 130.

In step 170, when the interface 28 outputs (e.g., audio and/or visually displays) another medical instruction, one or more of the LEDs 16b can optionally illuminate another portion of the storage compartment 16 of the container 12 to identify at least one independent medical product (e.g., same or different medical product) stored within the storage compartment 16 of the container 12. One or more previously illuminated LEDs 16b can optionally be darkened to darken portions of the storage compartment 16.

In step 180, the script ends. As illustrated by arrows "R1" and "R2," one more steps/instructions and/or entire scripts, or portions thereof can be repeated as desired.

In one exemplary use, container 12 is opened to trigger interface 28 to activate so that container 12 provides audio and visual assistance. In some embodiments, container 12 can be configured to open via an identity verification protocol. For instance, this can be done through a wide variety of approaches such as PIN numbers, scanning (e.g., code readers such as bar or Aztec codes on mobile device), RFID, biometrics (e.g., voice recognition, thumb print, retinal scan, etc.), key word or phrase, magnetic readers, ID's, cellular communication, a local or remote network, server, internet, app, etc.

Once opened, container 12 can be configured to output the following exemplary medical instructions or script via interface 28 with each instruction being output (e.g., displayed) independently of, and/or concomitantly with, one or more the other instructions:

1. "You have activated your Cardio Rescue. Please call 911 if not done so already. Please take 3 inhales of Oxygen and hit the forward arrow to continue."
2. "Take pill labeled 1, this is Nitroglycerin. Place under tongue and allow to dissolve. Take another 3 inhales of oxygen and press forward to continue."
3. "If you are still having pain, please take pill labeled 2. This is aspirin. Swallow all contents. Take another 3 inhales of oxygen and hit forward to continue."
4. "Please swallow pill labeled 3. This is a beta blocker. Take 3 inhales of oxygen and hit forward to continue."
5. "Please swallow pill labeled 4. This is a statin. Please swallow and take 3 inhales of oxygen. Please continue to take 3 inhales of oxygen until EMS arrives."

Further, a predetermined number or arrangement of lights 16b of container 12 can be illuminated to highlight a specific medical product corresponding a given instruction step such that the same and/or different portions of inserts or cutouts thereof are illuminated, while others are not.

The provided medical instructions/scripts and/or medical products 40 can be modified or customized for any suitable pathology. Scripts and/or medical products can be added to address patient-specific pathologies.

One exemplary smart safety kit can be in the form of a wound care kit that includes scripts for treating burns, lacerations, and abrasions (all OTC medical products). Example contents may include sterile strips, bacitracin, band-aides, burn cream, gauze, wrapping, tape, adhesive dressing, irrigation syringe, sterile water syringe, etc.

Another exemplary smart safety kit can be in the form of a pulmonary box that includes scripts to treat asthma, SOB, and COPD exacerbation. The pulmonary box can include prescription medical products such as an albuterol inhaler, Prednisone tablet (50 mg), a portable nebulizer, etc.

Yet another exemplary smart safety kit can be in the form of a diabetic box that includes scripts for hyperglycemia/hypoglycemia. The diabetic box can include prescription medical products and a customized aspect with a sliding scale. The diabetic box can include a glucometer, sugar tablets/liquid, glucagon, and/or pre-filled insulin.

Still another exemplary smart safety kit can be in the form of an allergy box that includes scripts to handle allergic reactions to bee stings, food allergies, and/or anaphylactic. The allergy box may have OTC and prescription forms. The allergy box can include epinephrine pre-filled syringe/auto injector, Benadryl tablets/liquid, anti-itch cream, Pepcid (20 mg), and/or steroid injectable (Decadron 10 mg IM injection).

One exemplary smart safety kit can be in the form of a baby sitter box that includes scripts for sickness, wound care, allergy, and SOB. The baby sitter box can include OTC and prescription forms. For instance, the baby sitter box can include all aspects of a wound car box, allergy box, and an SOB. Upon opening the container thereof, the user can choose which script to start. Sickness scripts may contain scripts for treating the stomach flu (e.g., vomiting/diarrhea), common cold (e.g., cough, sneeze, fever), etc. and can provide instructions for dosing.

Similarly, another exemplary smart safety kit can be in the form of a corporate box that can include all treatment options: cardio, pulmonary, allergy, wound care, diabetic, etc.

Other smart safety kits include, for example, an OBGYN box, an orthopedic box, a stroke box, a hospice box, etc.

Any of the presently disclosed boxes can be provided in travel form in which the containers can have a compact size and are usable with a smart device such as a smart phone, tablet, or laptop. An app configured to work with the travel boxes may be configured to work with or without internet connection.

Any of the presently disclosed containers can present as an aesthetically pleasing and/or multi-functional box. For instance, such boxes can present as alarm clocks, Wi-Fi radios, picture frames, etc.

Although multiple embodiments have been described, it should be recognized that these embodiments are not exclusive to each other and that features from one embodiment may be applied to others as desired.

Hereinafter, general aspects of implementation of the devices, systems and methods of the present disclosure will be described.

As used herein, "processing devices" or "processors" can include a "digital processing device," a "processing machine," a "computing device" such as "general purpose computer," and/or the like. For instance, suitable processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Suitable tablet computers include those with booklet, slate, and convertible configurations, known to those of skill in the art.

As noted above, the processing devices may include a general purpose computer. However, the processing devices described above may also utilize any of a wide variety of other technologies including a special purpose computer, a computer system including, for example, a microcomputer, mini-computer or mainframe, a programmed microprocessor, a micro-controller, a peripheral integrated circuit element, a CSIC (Customer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing the steps of the processes of the present disclosure.

As used herein, such processors can be understood to include at least one memory for storing data and/or instructions. The processing devices can indicate a specialized processor such as a microprocessor or central processing unit (CPU). The CPU is the electronic circuitry within a computer that carries out the instructions of a computer program by performing the basic arithmetic, logical, control and input/output (I/O) operations specified by the data and/or instructions. The data and/or instructions may be either permanently or temporarily stored in the memory or memories of the processing devices. The processing device executes the instructions that are stored in the memory or memories in order to process data. The set of instructions may include various instructions that perform a particular task or tasks, such as those tasks described herein. Such a set of instructions for performing a particular task may be characterized as a program, software program, or simply software.

As noted above, the processing device executes the instructions that are stored in the memory or memories to process data/information. This processing of data may be in response to commands by a user or users of the processor, in response to previous processing, in response to a request by another processor and/or any other input, for example.

The processors may utilize a suitable operating system configured to perform executable instructions. The operating system is, for example, software, including programs and data, which manages the device's hardware and provides services for execution of applications. Those of ordinary skill in the art will recognize that suitable server operating systems include, by way of non-limiting examples, FreeBSD, OpenBSD, NetBSD®, Linux®, Apple® Mac OS X Server®, Oracle® Solaris®, Windows Server®, and Novell® NetWare®. Those of ordinary skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of ordinary skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, Palm® WebOS®, etc.

In order to practice the method of the present disclosure described above, it is not necessary that the processor and/or the memory be physically located in the same geographical place. That is, the processor and the memory may be located in geographically distinct locations and connected so as to communicate in any suitable manner. Additionally, it is appreciated that the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Additionally, the memory may include two or more portions of memory in two or more physical locations.

To explain further, processing, as described above, is performed by various components and various memories. However, it is appreciated that the processing performed by two distinct components as described above may, in accordance with a further embodiment of the present disclosure, be performed by a single component. Further, the processing performed by one distinct component as described above may be performed by two distinct components. In a similar manner, the memory storage performed by two distinct memory portions as described above may, in accordance with a further embodiment of the present disclosure, be performed by a single memory portion. Further, the memory storage performed by one distinct memory portion as described above may be performed by two memory portions.

Further, various technologies may be used to provide communication between the various processors and/or memories, as well as to allow the processors and/or the memories of the present disclosure to communicate with any other entity; e.g., so as to obtain further instructions or to access and use remote memory stores, for example. Such technologies used to provide such communication might include a network, the Internet, Intranet, Extranet, LAN, an Ethernet, wireless communication via cell tower or satellite, or any client server system that provides communication, for example. Such communications technologies may use any suitable protocol such as TCP/IP, UDP, or OSI, for example.

As described above, a set of instructions may be used in the processing of the systems and devices of the present disclosure. The set of instructions may be in the form of a program or software. The software may be in the form of system software or application software, for example. The software might also be in the form of a collection of separate programs, a program module within a larger program, or a portion of a program module, for example. The software used might also include modular programming in the form of object oriented programming. The software tells the processing machine what to do with the data being processed.

Further, it is appreciated that the instructions or set of instructions used in the implementation and operation of the systems and devices of the present disclosure may be in a suitable form such that the processing device may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing device, e.g., to a particular type of computer, for example. The computer understands the machine language.

Any of the herein described methods, programs, algorithms or codes may be converted to, or expressed in, a programming language or computer program. The terms "programming language" and "computer program" or the like, include any language used to specify instructions to a processor, and include (but is not limited to) the following languages and their derivatives: Ada, APL, Assembler, Basic, Batch files, BCPL, C, C+, C++, COBOL, dBase, Delphi, Fortran, Java, JavaScript, machine code, Modula-2, operating system command languages, Pascal, Perl, PL1, Prolog, Python, REXX, Visual Basic, metalanguages which themselves specify programs, and all first, second, third, fourth, fifth, or further generation computer languages. Also included are database and other data schemas, and any other metalanguages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Further, it is not necessary that a single type of instruction or single programming language be utilized in conjunction with the operation of the presently disclosed systems and devices. Rather, any number of different programming languages may be utilized as is necessary and/or desirable The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

Also, the instructions and/or data used in the practice of present disclosure may utilize any compression or encryption technique or algorithm, as may be desired. An encryption module might be used to encrypt data. Further, files or other data may be decrypted using a suitable decryption module, for example.

It is to be appreciated that the data, instructions (or sets thereof), e.g., the software that enables the computer operating system to perform the operations described above may be contained on any of a wide variety of media or medium, as desired. Further, the data that is processed by the set of instructions might also be contained on any of a wide variety of media or medium. That is, the particular medium, e.g., the memory in the processing device, utilized to hold the set of instructions and/or the data used in accordance with present disclosure may take on any of a variety of physical forms or transmissions, for example. Illustratively, the medium may be in the form of paper, paper transparencies, a compact disk, a DVD, an integrated circuit, a hard disk, a floppy disk, an optical disk, a magnetic tape, a RAM, a ROM, a PROM, an EPROM, a wire, a cable, a fiber, a communications channel, a satellite transmission, a memory card, a SIM card, or other remote transmission, as well as any other medium or source of data that may be read by the processors of the present disclosure.

Further, the memory might be in the form of a database to hold data/information. The database might use any desired arrangement of files such as a flat file arrangement or a relational database arrangement, for example. The storage and/or memory may be one or more physical apparatus used to store data or programs on a temporary or permanent basis. In some embodiments, the device is volatile memory and requires power to maintain stored information. In some embodiments, the device is non-volatile memory and retains stored information when the processor is not powered. In some embodiments, the non-volatile memory includes flash memory. In some embodiments, the non-volatile memory includes dynamic random-access memory (DRAM). In some embodiments, the non-volatile memory includes ferroelectric random access memory (FRAM). In some embodiments, the non-volatile memory includes phase-change random access memory (PRAM). In some embodiments, the device is a storage device including, by way of non-limiting examples, CD-ROMs, DVDs, flash memory devices, magnetic disk drives, magnetic tapes drives, optical disk drives, and cloud computing based storage. In some embodiments, the storage and/or memory device is a combination of devices such as those disclosed herein.

In accordance with one aspect of the present disclosure, a variety of "user interfaces" may be utilized to allow a user to interface with the processing devices that are used to implement the present disclosure. As used herein, a user interface includes any hardware, software, or combination of hardware and software used by the processing device that allows a user to interact with the processing device. A user interface may be in the form of a dialogue screen for example. A user interface may also include any of a mouse, touch screen, keyboard, keypad, voice reader, voice recognizer, dialogue screen, menu box, list, checkbox, toggle switch, a pushbutton or any other device that allows a user to receive information regarding the operation of the processing device as it processes a set of instructions and/or provides the processing device with information/data. Accordingly, the user interface is any device that provides communication between a user and a processing device. The information provided by the user to the processing machine through the user interface may be in the form of a command, a selection of data, or some other input, for example.

As discussed above, a user interface (e.g., interface 28) is utilized by the processor that performs a set of instructions such that the processor processes data for a user. The user interface is typically used by the processor for interacting with a user either to convey information or receive information from the user. However, it should be appreciated that in accordance with some embodiments of the present disclosure, it is not necessary that a human user actually interact with a user interface used by the processing device of the present disclosure. Rather, it is also contemplated that the user interface of the present disclosure might interact, e.g., convey and receive information, with another processing device, robot, IoT device, etc., rather than a human user. Accordingly, the other processing device, IoT device, etc. might be characterized as a user. Further, it is contemplated that a user interface utilized in connection with the present disclosure may interact partially with another processing device, while also interacting partially with a human user.

In some embodiments, the processor includes a display (e.g., display 28*a*) to send visual information to a user. In some embodiments, the display is a cathode ray tube (CRT). In some embodiments, the display is a liquid crystal display (LCD). In some embodiments, the display is a thin film transistor liquid crystal display (TFT-LCD). In some embodiments, the display is an organic light emitting diode (OLED) display. In various some embodiments, on OLED display is a passive-matrix OLED (PMOLED) or active-matrix OLED (AMOLED) display. In some embodiments, the display is a plasma display. In some embodiments, the display is a video projector. In some embodiments, the display is interactive (e.g., having a touch screen or a sensor such as a camera, a 3D sensor, a LiDAR, a radar, etc.) that can detect user interactions/gestures/responses and the like. In still some embodiments, the display is a combination of devices such as those disclosed herein.

As can be appreciated, securement of any of the components of the presently disclosed apparatus can be effectuated using known securement techniques such welding, crimping, adhesion, fastening, etc.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. A smart safety kit, comprising:
    at least one medical product;
    a container configured to receive the at least one medical product therein, the container and the at least one medical product being separate and distinct;
    an interface coupled to the container;
    a processor; and
    a memory coupled to the container and including executable instructions stored thereon that, when executed by the processor, cause the interface to:
        determine that the container is opened; and
        send, based on the determination, an email or text message to an emergency contact, the email or text message including a digital map of a predefined area.

2. The self-help, smart safety kit of claim 1, wherein the instructions when executed further cause the interface to:
    receive input from the user; and
    output step-by-step medical instructions to enable the user to administer treatment with the at least one medical product.

3. The self-help, smart safety kit of claim 2, wherein the interface includes a display configured to output the step-by-step medical instructions.

4. The self-help, smart safety kit of claim 3, wherein the step-by-step medical instructions are output on the display with text, images, or combinations thereof.

5. The self-help, smart safety kit of claim 1, wherein the interface includes a speaker configured to output the step-by-step medical instructions.

6. The self-help, smart safety kit of claim 1, wherein the container includes a lid and a storage compartment, the lid configured to selectively enclose the at least one medical product within the storage compartment.

7. The self-help, smart safety kit of claim 6, wherein the lid is pivotally coupled to the storage compartment.

8. The self-help, smart safety kit of claim 6, wherein the lid is movable relative to the storage compartment from a closed position to an open position, the lid including a top surface and a bottom surface, the interface including a display, the bottom surface of the lid supporting the display such that the display is concealed when the lid is disposed in the closed position and exposed when the lid is disposed in the open position.

9. The self-help, smart safety kit of claim 1, further comprising a power supply that is operatively coupled to the processor to power the processor, the interface, the memory, or combinations thereof.

10. The self-help, smart safety kit of claim 1, wherein the at least one medical product includes a first independent medical product and a second independent medical product, wherein the container includes an insert that fits in a storage compartment of the container, the insert defines a first cavity and a second cavity, the first cavity is configured to removably support the first independent medical product therein and the second cavity configured to removably support the second independent medical product therein.

11. The self-help, smart safety kit of claim 1, wherein the processor is configured to communicate with a remote network.

12. The self-help, smart safety kit of claim 1, wherein the email or text message further includes a location indicator that indicates a specific location of the smart safety kit in the predefined area.

13. A method for facilitating medical treatment for a user with a smart safety kit, the method comprising:
    removably supporting at least one independent medical product in a storage compartment of a container of the smart safety kit;

receiving input, through an interface of the container, from the user;

outputting step-by-step medical instructions through the interface of the container to enable the user to administer the medical treatment with the at least one independent medical product;

determining that the container is opened; and sending, based on the determination, an email or text message to an emergency contact upon an activation of the smart safety kit, the email or text message including a digital map of a predefined area and a location indicator that indicates a specific location of the smart safety kit in the predefined area.

14. The method of claim 13, wherein the predefined area is a school.

15. The method of claim 13, further comprising outputting at least one step of the step-by-step medical instructions in response to the input received from the user.

16. The method of claim 13, wherein outputting the step-by-step medical instructions through the interface of the container includes displaying the step-by-step medical instructions on a display of the interface.

17. The method of claim 16, wherein displaying the step-by-step medical instructions includes displaying text, images, or combinations thereof on the display.

18. The method of claim 13, wherein outputting the step-by-step medical instructions through the interface of the container includes emitting sound through a speaker of the interface.

19. The method of claim 13, outputting the step-by-step medical instructions through the interface of the container includes emitting sound through a speaker of the interface and displaying the step-by-step medical instructions on a display of the interface.

20. The method of claim 13, further comprising electrically powering the interface.

21. The method of claim 13, further comprising enabling the container to communicate with a remote network.

22. A self-help, smart safety kit, comprising:

at least one medical product;

a container configured to receive the at least one medical product therein; and an interface coupled to the container, the interface configured to receive input from a user for communication with the user, wherein the container is configured to activate based on input received by the user, wherein the interface includes instructions stored thereon, which when executed by a processor, determines that the container is opened, sends, based on the determination, an email or text message to an emergency contact when the container is activated, the email or text message including a digital map of a school and a location indicator that indicates a room number of the smart safety kit in the school.

* * * * *